United States Patent [19]

Ashton et al.

[11] Patent Number: 4,739,113
[45] Date of Patent: Apr. 19, 1988

[54] BIS(CYCLOPROPANECARBOXAMIDO)AL-KADIENEDIOIC ACIDS AS RENAL DIPEPTIDASE INHIBITORS

[75] Inventors: Wallace T. Ashton, Clark; Anna Chen, Rahway; Edward F. Rogers, Middletown, all of N.J.

[73] Assignee: Merck & Co., Inc., Rahway, N.J.

[21] Appl. No.: 868,472

[22] Filed: May 30, 1986

[51] Int. Cl.$^4$ ................ C07C 103/737; A61K 31/215; A61K 31/19
[52] U.S. Cl. .................................... 562/500; 560/118
[58] Field of Search ........................ 562/500; 560/118; 514/531, 563

[56] References Cited

U.S. PATENT DOCUMENTS 4,406,902  9/1983  Ashton et al. ...................... 514/269
4,539,208  9/1985  Kahan et al. ........................ 514/195

FOREIGN PATENT DOCUMENTS 0010573  10/1983  European Pat. Off. .

OTHER PUBLICATIONS

Hynes et al, Journal of Med. Chem., 15, 1332–1333 (1972).
Ashton et al, 20th Interscience Conference on Antimicrobial Agents & Chemotherapy, New Orleans, La., Sep. 22–24, 1980.
Journal of Theoretical Biology, vol. 109, pp. 471–474, (1984), Rogers.

*Primary Examiner*—Donald B. Moyer
*Assistant Examiner*—Patricia M. Scott
*Attorney, Agent, or Firm*—Robert J. North; Hesna J. Pfeiffer; Julian S. Levitt

[57] ABSTRACT

Novel chemical compounds are provided which selectively inhibit the metabolism of renal dipeptidase (E.C.3.4.13.11) and therefore are useful in combination with antibacterial products. These chemical compounds are (Z,Z)-α,α'-bis(2,2-disubstituted cyclopropanecarboxamido)-α,α'-alkadienedioic acids.

7 Claims, No Drawings

BIS(CYCLOPROPANECARBOXAMIDO)AL-KADIENEDIOIC ACIDS AS RENAL DIPEPTIDASE INHIBITORS

BACKGROUND OF THE INVENTION

A new class of fused ring β-lactam antibiotics, including thienamycin and its semisynthetic derivatives, epithienamycins, and olivanic acids, has recently been described. These compounds which will be defined more extensively below, are hereinafter referred to as the "thienamycin class of compounds". These compounds have a high level of antibacterial activity, but are subject to extensive metabolism by mammalian species.

The kidney was identified as the primary site of metabolism, and an enzyme was purified from renal extracts which catalyzed the inactivation of thienamycin by hydrolysis of the β-lactam. By such criteria as cytological localization, substrate specificity and susceptibility to enzyme inhibitors, this enzyme is very similar if not identical to a widely studied renal dipeptidase (E.C.3.4.13.11), also referred to in the literature as "dehydropeptidase peptidase I". However, the β-lactamase activity is exhibited only toward the thienamycin class of compounds. Indeed, there exists no precedent example of the mammalian metabolism via β-lactam cleavage of any representative of the classical β-lactam antibiotics, the penicillins and cephalosporins.

DETAILED DESCRIPTION OF THE INVENTION

The chemical substances which selectively inhibit the metabolism of the dipeptidase (E.C.3.4. 13.11), also called "dipeptidase inhibitors", include chemical compounds which are bis-substituted alkadienedioic acids having the following formula:

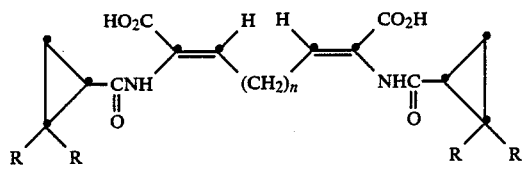

wherein n is an integer from 1 to 10, R is $C_1$–$C_4$ lower alkyl or halo, and the $C_{1-6}$ esters, pharmaceutically acceptable salts, racemates and diastereomers thereof.

The preferred configuration at the cyclopropyl center is S, although the R,S-mixture is also contemplated within the scope of this invention.

The most preferred compounds are those in which n is 6, and R is $CH_3$, Br or Cl, in the S-configuration.

The Z configuration (J. E. Blackwood et al., *J. Am. Chem. Soc.*, 90, p. 509 (1968)) is assigned to the above compounds on the basis of their NMR spectra by analogy with the work of A. Srinavasan et al., Tetrahedron Letters, 891 (1976).

Although these compounds of Formula I, when $R^1$ is H, are described and named as the free acids, it will be apparent to one skilled in the art that various pharmaceutically acceptable derivatives such as alkali and alkaline earth metal, ammonium, or amine salts or the like can be employed as equivalents thereto. Salts such as the sodium, potassium, calcium or tetramethylammonium salts are suitable.

UTILITY OF THE INVENTION

As noted above, the compounds of this invention are dipeptidase (E.C.3.4.13.11) inhibitors, and can be used in combination with antibacterial compounds which are subject to renal degradation. The group of antibiotics of present primary importance for use in combination with the (Z,Z)-bis-(2,2-disubstituted cyclopropanecarboxamido)alkadienedioic acids of this invention are the "thienamycin class of compounds".

The term "thienamycin class of compounds" is used to identify any of a number of naturally occurring, semi-synthetic or synthetic derivatives or analog compounds having a common fused-ring β-lactam nucleus. These compounds can be generically classed as 6- and (optionally) 2-substituted pen-2-em-3-carboxylic acids and 1-carbadethia-pen-2-em-3-carboxylic acids or 1-azabicyclo[3.2.0]hept-2-ene-7-one-2-carboxylic acids.

Specific compounds particularly useful in this invention are represented structurally in the following formula II:

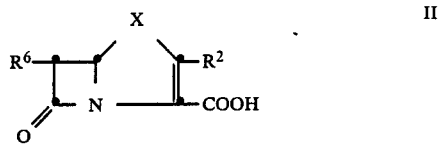

wherein X can be $CH_2$ or S; $R^2$ can be hydrogen; S-alkyl wherein the alkyl group is from 1 to 6 carbons; $SCH_2CH_2NHR^3$, wherein $R^3$ is hydrogen, acetyl, formimidoyl, acetimidoyl; $-S(O)-CH=CHNHCOCH_3$ and $-S-CH=CHNHCOCH_3$; and $R^6$ is

wherein $R^7$ is hydrogen, hydroxy or sulfonyloxy, or $R^6$ is H as described and claimed in U.S. Pat. No. 4,539,208, hereby incorporated by reference. All possible stereoisomeric forms are included within the above structural definition.

All of these compounds with Formula II are described in the literature. When X is $CH_2$ and $R^2$ is $SCH_2CH_2NH_2$ and $R^6$ is $CH(OH)CH_3$, the compound is known as thienamycin, an antibiotic produced by fermentation of *S. cattleya*, described and claimed in U.S. Pat. No. 3,950,357, issued April 13, 1976. The N-substituted derivatives of thienamycin, i.e., in the formula II above wherein R is other than hydrogen, are disclosed and claimed in co-pending U.S. applications and their published foreign equivalents. The fermentation product N-acetyl thienamycin ($R^6$ is $CH(OH)CH_3$, and $R^3$ is acetyl), also called 924A, is claimed in Belgian Patent No. 848,346, issued May 16, 1977. The N-imidoyl derivatives are covered in Belgian Patent No. 848,545, issued May 20, 1977. The unsaturated side chain-containing compound, also called N-acetyl-dehydrothienamycin or $924A_5$ is a fermentation product claimed in U.S. Pat. No. 4,162,323 and also in Belgian Patent No. 866,035, issued Oct. 17, 1978. Epimeric forms of N-acetyl thienamycin, also called $890A_1$ and $890A_3$, as well as desacetyl $890A_1$ and desacetyl $890A_3$ are disclosed, respectively in published French Patent No. 76 34887, issued Apr. 25, 1980, claiming priority of U.S. Ser. No. 634,300, filed Nov. 21, 1975, now abandoned, in favor of continuation application Ser. No. 827,504, issued as U.S. Pat. No. 4,162,324 and Belgian Patent No. 848,349, issued May 16, 1977. Epimeric forms of the unsaturated thienamycin, also called 890A$_2$ and 890A$_5$ are claimed in published French Patent No. 77 11891 granted Apr. 20, 1977 claiming priority of U.S. Ser. No. 680,331 filed April 28, 1976 now abandoned in favor of continuation application Ser. No. 823,258, now U.S. Pat. No. 4,141,986. The 6-sulfonyloxy containing N-acetyl compounds, also called 890A$_9$ or 890A$_{10}$ are claimed respectively, in published French Patent No. 77 34456, granted June 23, 1980 claiming priority of U.S. Ser. No. 742,957 filed Nov. 17, 1976, now abandoned in favor of Ser. No. 891,799, which was abandoned in favor of Ser. No. 79,122, now U.S. Pat. No. 4,264,736 and published French Patent No. 77 34457, granted Mar. 3, 1980, claiming priority of U.S. Ser. No. 742,958 filed Nov. 17, 1976. Desacetyl analogues of 890A$_9$ and 890A$_{10}$ are respectively claimed in U.S. Ser. No. 767,723, filed Feb. 11, 1977, now abandoned, and its continuation U.S. Ser. No. 860,665, filed Dec. 15, 1977, now abandoned, and also in French Patent No. 78 03666 granted May 5, 1978; and U.S. Ser. No. 767,920, filed Feb. 11, 1977, now abandoned, and its continuation U.S. Ser. No. 006,959, filed Jan. 15, 1979, now abandoned, and also in French patent application No. 78 03667, filed Feb. 9, 1978. Some of these latter compounds in the 890A$_9$ and 890A$_{10}$ series are also known as derivatives of olivanic acid (see Corbett et al., *J. Chem. Soc. Chem. Commun.*, 1977, No. 24, pp. 953–54). Compounds of the Formula I above when R$^2$ is hydrogen, also called descysteaminyl thienamycins, are claimed in U.S. Ser. No. 668,898, filed Mar. 22, 1976, now abandoned and its continuation-in-part, U.S. Ser. No. 847,297, filed Oct. 31, 1977, now abandoned, and also in Belgian Patent No. 867,227, granted Nov. 20, 1978.

When R$^6$ is hydrogen, and X is CH$_2$, these compounds are disclosed in U.S. Ser. No. 843,171, filed Oct. 19, 1977, abandoned in favor of Ser. No. 109,737, now U.S. Pat. No. 4,543,257 and in Belgian Patent No. 860,962, granted May 18, 1978.

A thienamycin type antibiotic in which R$^2$ is SCH$_2$CH$_2$NHAc and R$^6$ is C$_2$H$_5$, has been named PS5 and is reported by K. Okaimura et al., *J. Antibiotics*, 31, p. 480 (1978), see also Belgian Patent No. 865,578.

The compounds in which X is S, also called "penems", are described by R. B. Woodward in "Recent Advances in the Chemistry of β-Lactam Antibiotics", J. Elks (Ed.), The Chemical Society, London, 1977, p. 167; R. B. Woodward, Abstracts of Uppsala University 500 Years Symposium on Current Topics in Drug Research, Uppsula, Sweden, Oct. 19–21, 1977. Acta. Pharm. Suecica. vol. 14, Supplement, p. 23, and U.S. Pat. Nos. 4,070,477, issued Jan. 24, 1978 and 4,260,618 issued Apr. 7, 1981, and in British Patent application Nos. 2,013,674 published Aug. 15, 1979 and 2,042,520 published Sept. 24, 1980. The compounds wherein X is S are not limited to those encompassed by formula I above but include, in addition, all of the compounds disclosed in the references listed in this paragraph.

The disclosures of the foregoing patents, pending and abandoned patent applications and literature references are hereby incorporated by reference.

Particularly preferred members within the thienamycin class of compounds are the N-formimidoyl and N-acetamidoyl derivatives of thienamycin. The crystalline form of N-formimidoyl thienamycin, which has recently been described, is also useful in the practice of this invention. An example illustrating a preferred way of making this compound follows:

ILLUSTRATIVE EXAMPLE

N-Formimidoyl thienamycin, (NFT) crystalline

Step A: Benzylformimidate hydrochloride

A 3 liter three-necked flask fitted with an addition funnel, overhead stirrer, and a reflux condenser, was charged with a mixture of benzyl alcohol (125 g, 1.15 mol) formamide (51 g, 1.12 mol) and anhydrous ether (1200 ml). The mixture was stirred vigorously at room temperature (20°–25° C.) under a nitrogen atmosphere and benzoyl chloride (157 g, 1.12 mol) in 50 ml of anhydrous ether was added dropwise using the addition funnel. The addition required approximately 50 minutes.

The reaction mixture was stirred and additional 60 minutes at room temperature. The ether was removed by decantation and 300 ml of acetic anhydride in 500 ml of anhydrous ether was added. The mixture was stirred 30 minutes at room temperature. The precipitate was allowed to settle and the ether-acetic anhydride was again removed by decantation. The solid was collected by filtration, washed with 500 ml of ether and dried in vacuo over KOH at 25° C. for 2 hours to give 130 g (67%) of benzylformimidate hydrochloride as a white solid.

The product was assayed by NMR $\delta$ (DMSO) 5.7 (s, 2H, $\phi$CH$_2$), 7.5 (s, 5H, $\phi$), 9.0 (s, 1H, HC=N). The product is thermally unstable. It decomposes to formamide and benzyl chloride at 0° C. and above. However, no appreciable decomposition was detected on storage at −20° C. for 2 months.

Step B: Derivatization of Thienamycin

Thienamycin (in the form of a 6 liter aqueous solution, pH=6.5, concentrate from the fermentation broth, containing 28 g thienamycin) was placed in a large beaker (121) and cooled to 0° C. The beaker was equipped with a pH meter and an efficient high speed stirrer. The pH was raised to 8.5 by the careful addition of 3N KOH (KOH was added dropwise via syringe to the stirred solution). The solution was treated with 6 equivalents of solid benzyl formamidate hydrochloride (100 g) in portions while maintaining the pH at 8.5±0.3 by the addition of 3N KOH (200 ml) using a syringe. The addition required 3–5 minutes. The reaction mixture was stirred for 6 minutes at 0° C. and then assayed by liquid chromatography to insure completion of the reaction. The solution was adjusted to pH 7 with 1N HCl. The volume of the reaction mixture was measured, and the solution was assayed by UV. The neutralized reaction mixture was concentrated to 15 g/l on the reverse osmosis unit at 10° C. The volume of the concentrate was measured and the pH was adjusted to 7.2–7.4, if necessary. The concentrate was filtered through a medium porosity sintered glass funnel to remove any solids present after concentration.

Step C: Dowex 50W×2 Chromatography

The concentrate (750–1000 ml, 15–20 g) was applied to 0° C. to a precooled 18.1 column of Dowex 50W×2 in the potassium cycle (200–400 mesh resin) and the column was eluted at 0°–5° C. with distilled deionized water a flow rate of 90 ml/min and a head pressure of 0–45 psig.

Forerun fractions of 4 liter, 2 liter and 1 liter were collected followed by 18 fractions of 450 ml each, and one final fraction of 2 liter. Each fraction was assayed by UV (1/100 dilution, NH$_2$OH extinction was omitted) and the total amount of NFT present in each fraction was calculated. The beginning and end fractions were assayed for liquid chromatography purity and the desired rich cut fractions were combined. The PH of the combined rich cuts was determined by both pH meter and bromothymol blue indicating solutions and was adjusted to pH 7.2–7.4 if necessary. The combined rich cuts (3–4 liter) were then assayed by UV and the total formamidine content was determined, 15–16 g, 75% yield from the column. The rich cuts were concentrated on the reverse osmosis unit at 10° C. as far as possible, then the concentration to 33 g/liter was completed on the circulatory evaporator at less than 28° C. A total volume of about 500 ml concentrate was obtained.

Step D: Crystallization of N-Formimidoyl Thienamycin

The concentrate from the previous step is adjusted to 7.3, if necessary, and N-formimidoyl thienamycin content assayed by UV, was about 85–90%. The concentrate was filtered through a sintered glass funnel (medium porosity) into a large Erlenmeyer flask. Five volumes ( 2200 ml) of 3A ethanol was filtered into the concentrate and the solution was stirred at room temperature for 10 minutes and at 0° C. for 12–24 hours.

The crystals were filtered by suction filtration and washed with 0.1 volume ( 250 ml) of 0° C. 80% 3A ethanol followed by 1/25 volume (100 ml) of 3A ethanol at room temperature. The crystals were dried in vacuo for 12–24 hours to give approximately a 40% overall yield of N-formimidoyl thienamycin (10–12 g).

Analytical results on a 50 g blend of N-formimidoyl thienamycin, prepared as above, are as follows:

C, theory 45.42%; found, 45.82%; H, theory 6.03%; found, 5.72%; N, theory 13.24%; found, 13.10%; S, theory 10.10% found, 10.14%; residue on ignition, predicted 0.5, found 0.47%.;

$[\alpha]D^{25}=89.4°$, T.G.=6.8%, UV $\lambda$max 300 MM, E%=328.

METHOD OF USING THE INVENTION

As mentioned above, the thienamycin-type compound is used in combination with the dipeptidase inhibitor.

The combination of the novel chemical inhibitors of this invention and the thienamycin class compound can be in the form of a pharmaceutical composition containing the two compounds in a pharmaceutically acceptable carrier. The two can be employed in amounts so that the weight ratio of the thienamycin class compound to inhibitor is 1:3 to 30:1, and preferably 1:1 to 5:1.

The components can also be separately administered. For instance, the thienamycin class compound can be administered intramuscularly or intravenously in amounts of 1–100 mg/kg/day, preferably 1–20 mg/kg/day, or 1–5 mg/kg/day, in divided dosage forms, e.g., three or four times a day. The inhibitor can be separately administered, orally, intramuscularly, or IV, in amounts of 1–100 mg/kg/day, or preferably 1–30 mg/kg/day, or 1–5 mg/kg/day. The amounts of the two components administered during one day ideally are within the ratio limits denoted above.

One preferred dosage form known to applicants is as a single dose, of two compounds, one being N-formimidoyl thienamycin and the other being (Z,Z)-2,11-bis(2,2-dimethylcyclopropanecarboxamido)-2,10-dodecadienedioic acid, co-administered in a sterile aqueous IV injection form (sodium salt), at a level of 150 mg of the thienamycin and either 7 or 150 mg of the dipeptidase inhibitor. This dose is given to humans (each assumed to weigh about 80 kg) from 1 to 4 times a day, or 2–8 mg/kg/day of the thienamycin class compound and 1–8 mg/kg/day of the inhibitor. The thienamycin can also be administered at either 250 or 500 mg together with the inhibitor at 1:1 (weight) ratio, or 250 or 500 mg also. When the dosage is given 1–4 time daily, from 3.1–25 mg/kg/day is given of each component.

The components, whether administered separately or together are employed in pharmaceutically acceptable carriers such as conventional vehicles adapted for oral administration such as capsules, tablets, or liquid solutions or suspensions. The components separately or together, can also be dissolved in a vehicle adapted for administration by injection. Suitable formulations for oral use, may include diluents, granulating agents, preservatives, binders, flavoring agents, and coating agents. The example of an oral use composition in the combination of active ingredients, or the acid component alone, intermixed in the dry pulverulent state with gelatin, starch, magnesium stearate, and alginic acid, and pressed into a tablet.

As noted above, the presently known preferred method is parenteral administration of the thienamycin class compound and either co-parenteral administration or oral administration of the inhibitor compound.

METHODS OF TESTING THE COMBINATION ANTIBACTERIAL AGENT

As noted, disposition studies with thienamycin, its natural analogs and its semisynthetic derivatives have revealed a major metabolic degradation pathway of elimination in the various species examined (mouse, rat, dog, chimpanzee, Rhesus monkey). The extent of metabolism is reflected in low urinary recovery and short plasma half-lives. The nature of this degradation was demonstrated to be lacta cleavage by the renal dipeptidase (E.C.3.4.13. 11), described first by Bergmann, M. and Schleich, H., Z. Physiol. Chem., 205 65 (1932); see also Greenstein, J. P., Advances in Enzymology, Vol. VIII, Wiley-Interscience, (1948), New York, and Campbell, B. J.; Lin, Y. C., Davis, R. V and Ballew, E., "The Purification and Properties of Particulate Renal Dipeptidase", Biochim. Biophys. Acta., 118, 371 (1966).

In order to demonstrate the ability of the compounds of Formula I to suppress the action of the renal dipeptidase enzyme, an in vitro screen procedure was followed. This measured the ability of compounds to inhibit hydrolysis of glycyldehydrophenylalanine (GDP) by a solubilized preparation of dipeptidase isolated from hog kidneys. The procedure is as follows: to a 1 ml system containing 50 mM "MOPS" (3-(N-morpholino)-propanesulfonic acid) buffer, pH 7.1, is added 5 μg of lyophilized enzyme, and the test compound at a final concentration of 0.1 mM. After a five minute incubation at 37° C., GDP is added to a final concentration of 0.05 mM. Incubation is continued for 10 minutes at 37° C. and hydrolysis of GDP is measured by the change in optical density with time at 275 nm. Inhibition of the optical density with time at 275 nm. Inhibition of the enzyme is gauged by comparison to a standard run containing no inhibitor and is expressed as the inhibitor binding constant, $K_i$. This is the concentration of the inhibitor which achieves 50% inhibition of enzyme.

The substrate GDP is employed in preference to thienamycin in this screen because it has a much higher maximal velocity of hydrolysis by renal dipeptidase, thereby reducing the amount of enzyme required. Both GDP and thienamycin have a similar affinity for renal dipeptidase; furthermore, $K_i$'s of inhibitors tested have been identical for the two substrates.

Urinary recovery of thienamycin is measured in all cases with the use of a cylinder or disc diffusion assay, conducted in a manner described in U.S. Pat. No. 3,950,357. This bioassay, with *Staphylococcus aureus* ATCC 6538 as the test organism, has a useful response range from 0.04 μg/ml to 3.0 μg/ml.

METHODS OF PREPARING THE TITLE COMPOUNDS

These bis compounds are prepared by condensation of an α,α'-dioxoalkanedioic acid with approximately two equivalents of a 2,2-disubstituted cyclopropanecarboxamide by heating in an inert solvent such as toluene. Water liberated during the condensation may be removed by use of a Dean-Stark trap or other means. The diketo diacids may be prepared by various methods known in the literature for the synthesis of α-keto acids. A preferred method, used in our example, involves reaction of an α,Ω-dihaloalkane with the sodium salt of ethyl 1,3-dithiane-2-carboxylate to give a bis(1,3-propylenedithioketal), which is deprotected with aqueous N-bromosuccinimide (or other literature methods) to give the diketo diester. Saponification of the diester followed by acidification yields the desired α,α'-dioxoalkanedioic acid.

EXAMPLE

Preparation of (Z,Z)-2,11-bis(2,2-dimethylcyclopropanecarboxamido)-2,10-dodecadienedioic acid

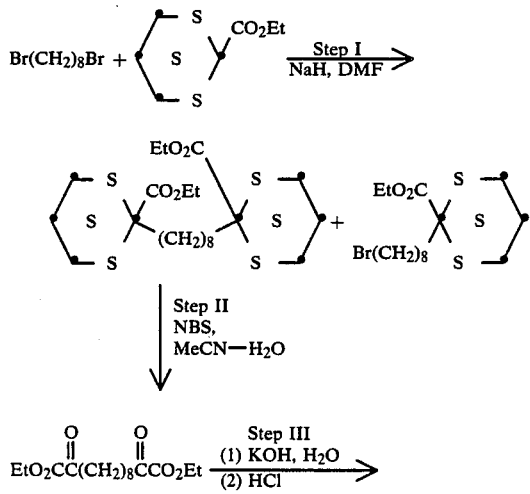

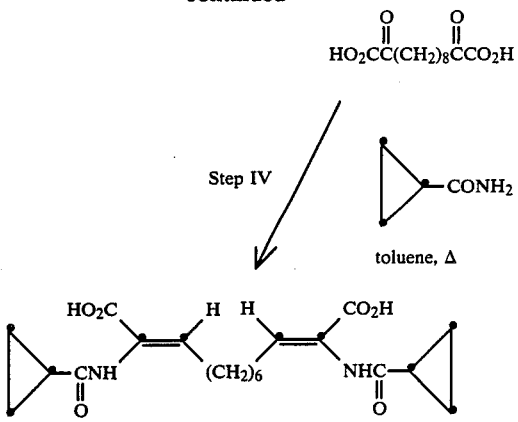

Step A: Bis(1,3-propylenedithioketal) of diethyl 2,11-dioxododecanedioate

To a well-stirred suspension of 3.4 g (80 mmole) of sodium hydride (57% dispersion in oil) in 140 ml of dry toluene cooled to 5° C. in an ice bath was slowly added a solution of 10.9 g (40 mmole) of 1,8-dibromooctane and 15.3 g (80 mmole) of ethyl 1,3-dithiane-2-carboxylate in 40 ml of DMF. The mixture (protected from moisture) was stirred in the ice bath for 1 hour and then at room temperature for 3 days. It was then combined with the reaction mixture of a similar run on the same scales. The toluene layer of the combined mixtures was separated, washed twice with water, dried over sodium sulfate, and filtered. Concentration of the filtrate gave 46 g of residual oil. Purification of this material by preparative high pressure liquid chromatography (HPLC) (elution with 10:1 hexane-ethyl acetate) yielded 15.4 g of the bis(1,3-propylenedithioketal) of diethyl 2,11-dioxododecanedioate (eluted first), along with 12.1 g of ethyl 2-(8-bromooctyl)-1,3-dithiane-2-carboxylate (eluted subsequently). The products were identified by NMR spectrometry.

Step B: Diethyl 2,11-dioxododecanedioate

A solution of 4.9 g (10 mmole) of the bis(1,3-propylenedithioketal) from Step A in 40 ml of acetonitrile was added all at once to a mixture of 21.4 g (120 mmole) of N-bromosuccinimide, 160 ml of acetonitrile, and 40 ml of water stirred at 0° C. An immediate exotherm caused the temperature to rise to 15° C., as the solution turned red and then orange. After the exotherm had subsided, an additional 3.5 g (20 mmole) of N-bromosuccinimide was added, and the solution was stirred for an additional 10 minutes at 5° C. An excess of saturated aqueous sodium bisulfite solution was added to the mixture, and the product was extracted with 400 ml of 1:1 hexane-methylene chloride. The organic phase was washed successively with saturated sodium bicarbonate solution, water, and saturated sodium chloride solution. The dried organic solution was concentrated. The residue was taken up in methylene chloride, washed again with water, dried over sodium sulfate, and filtered. Concentration of the filtrate gave 3 g of oily product, which showed satisfactory purity by TLC (10:1 hexane-ethyl acetate) and was used in the next reaction without further purification.

Step C: 2,11-Dioxododecanedioic acid

A suspension of 350 mg (1.11 mmole) of diethyl 2,11-dioxododecanedioate in 10 ml of 5% potassium hydroxide solution was stirred at room temperature for 2 hours, by which time all of the material had gone into solution. The aqueous solution was acidified with concentrated HCl, and the product was extracted with ethyl acetate. The ethyl acetate phase was washed with water, dried over sodium sulfate and filtered. Concentration of the filtrate gave 250 mg of residue, which solidified. This material was used directly in the next reaction without purification.

Step E: (Z,Z)-2,11-bis(2,2-dimethylcyclopropane-carboxamido)-2,10-dodecadienedioic acid To a suspension of 250 mg (0.97 mmole) of crude 2,11-dioxododecanedioic acid from Step C in 20 ml of toluene was added 200 mg (1.77 mmole) of 2,2-dimethylcyclopropanecarboxamide. The mixture was stirred under reflux for 18 hours. The resulting solution was cooled to room temperature, whereupon a second phase separated. After decantation of the toluene, the semi-solid residue was crystallized from ethyl acetate to give 36 mg of solid with m.p. 188–190° C. The material ran as a single spot ($R_f$ 0.5) in 4:1 toluene-acetic acid. NMR and mass spectra were consistent with the assigned structure.

Analysis calc'd for: $C_{24}H_{36}N_2O_6 \cdot 0.5H_2O$:
C, 63.00; H, 8.15; N, 6.12.
Found: C, 63.39; H, 8.02; N, 5.71.

What is claimed is:

1. A compound of the formula:

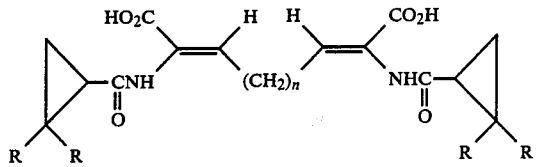

in the Z,Z-configuration wherein n is an integer from 1 to 10, R is $C_1$–$C_4$ lower alkyl or halo or the $C_{1-6}$ alkyl ester, pharmaceutically acceptable salt, racemate, or diastereomer thereof.

2. The compound of claim 1 wherein R is $CH_3$, Cl or Br.

3. The compound of claim 1 wherein n is 4–6.

4. The diastereomerically mixed form: S,S; S,R; R,R; of the compound of claim 1.

5. The S,S- form of the compound of claim 1.

6. The compound of claim 1 wherein n is 6 and R is methyl.

7. The compound of claim 1 which is (Z,Z)-2,11-bis(2,2-dimethylcyclopropanecarboxamido)-2,10-dodecadienedioic acid.

* * * * *